United States Patent [19]

Holick

[11] 4,310,511

[45] Jan. 12, 1982

[54] SUNSCREEN COMPOSITIONS CONTAINING $\Delta^{5,7}$STEROIDAL DIENES

[75] Inventor: Michael F. Holick, Sudbury, Mass.

[73] Assignee: Massachusetts General Hospital, Boston, Mass.

[21] Appl. No.: 193,297

[22] Filed: Oct. 2, 1980

[51] Int. Cl.³ .................... C07J 7/00; A01N 45/00; A61K 7/42; A61K 7/44
[52] U.S. Cl. .................................. 424/59; 424/238; 424/60; 260/397.2
[58] Field of Search .................... 424/59, 238, 242; 260/397.2

[56] References Cited

U.S. PATENT DOCUMENTS 3,479,428  11/1969  Bryce et al. ................... 424/59
4,115,547  9/1978  Degen et al. .................. 424/59

FOREIGN PATENT DOCUMENTS 1540187  8/1968  France ........................ 424/59

Primary Examiner—Elbert L. Roberts
Attorney, Agent, or Firm—Oblon, Fisher, Spivak, McClelland & Maier

[57] ABSTRACT

A sunscreening composition which comprises a sunscreening amount of an opacifying agent and a therapeutic amount of a $\Delta^{5,7}$ steroidal diene which is non-hydroxylated at any of positions 1; 1,25; 1,24,25 or 1,25,26 thereof.

8 Claims, 1 Drawing Figure

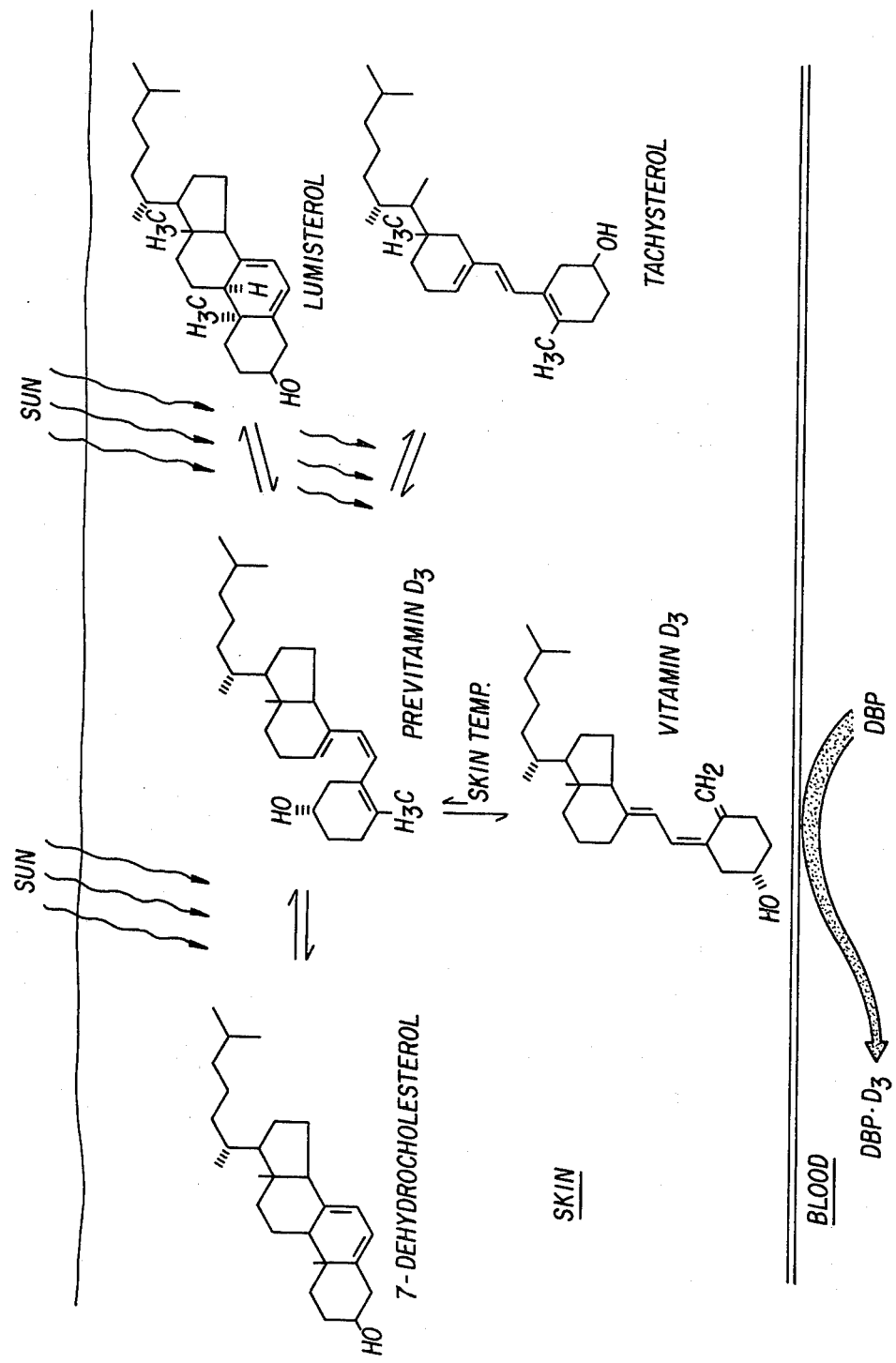

SUNSCREEN COMPOSITIONS CONTAINING Δ$^{5,7}$STEROIDAL DIENES

BACKGROUND OF THE INVENTION

1. Field of the Invention

The present invention relates to sunscreen compositions and methods of protecting the skin from ultraviolet radiation.

2. Description of the Prior Art

Sunscreens are used in the prevention of sunburns. The region of the sunlight which a compound must absorb in order to be an effective sunscreen is dependent on the intensity and wavelength of the solar radiation, and the body's erythemic response to the light. Insignificant amounts of solar radiation reach the earth's surface below 290 nm. The shorter wavelengths are screened out by the atmosphere. On the other hand, studies on the erythema produced by ultraviolet light on untanned human skin indicate a maximal erythemagenic effect at 254 nm and at 287 nm, separated by a minimum at 280 nm. Only the second maximum is within the solar radiation region. It is possible to use these facts to establish what has been called a "sunburn curve." Plotting the solar radiation curve and the erythema curve on the same graph, a sunburn curve can be constructed by multiplying the ordinates of the erythema curve by those of the solar radiation curve for each wavelength. Doing this, it has been reported that maxima in the sunburn curve appear at 304 nm, or are in the range of 290–326 with a maximum at 308 nm. (see for example Riegelman and Penna, *Journal of the Society of Cosmetic Chemists*, volume 11, 280–289 (June, 1960)).

In order to be a good sunscreen, a compound must possess high absorption properties at 290–310 nm while superimposing on the sunburn curve.

Normally used sunscreening compounds, such as p-aminobenzoic acid (PABA) or benzophenones meet, to some extent or other, the absorption requirements.

The use of sunscreen compounds which block light in the region 290–310 nm, while effective for preventing sunburn, has the undesirable consequence of blocking the precise radiation wavelength needed to transform 7-dehydrocholesterol, the precursor of vitamin $D_3$ known to exist in the skin, into vitamin $D_3$. Under normal radiation conditions, with photolysis at 250–320 nm, 7-dehydrocholesterol undergoes ring opening to previtamin $D_3$ (1) (*Holick, M.F. et al,* Biochem.Biophys.Res.Comm., 76: 107–114(1977)):

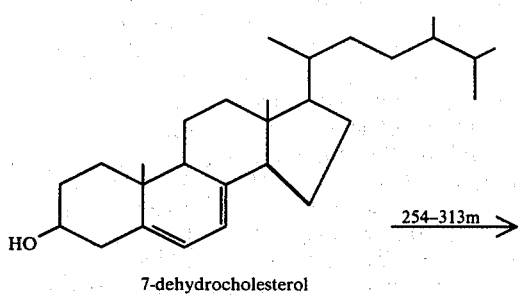

7-dehydrocholesterol

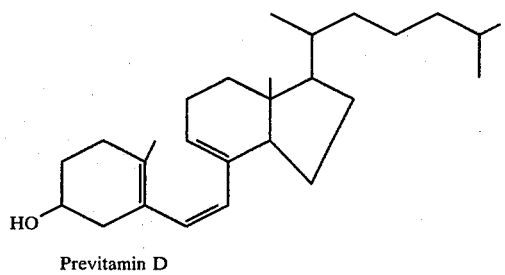

Previtamin D

By a dark, thermally induced sigmatropic shift, the previtamin is then converted to Vitamin D (2):

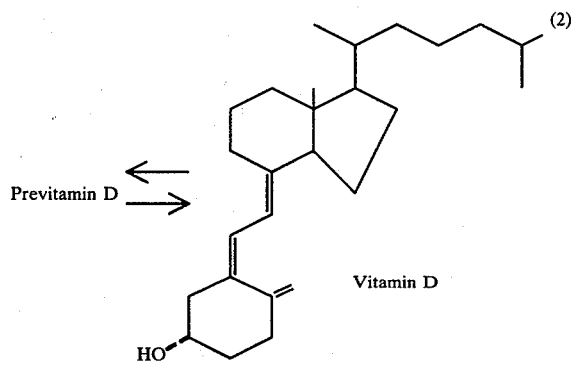

The availability of vitamin D precursors in the skin and their photo-induced transformation to previtamin D, and then to vitamin D, is an efficient physiological source of, and mechanism for the replenishment of vitamin D. However, when sunscreen compounds which block radiation in the ultraviolet region 250–320 nm are used, this replenishment mechanism is blocked. The result is the possibility of serious vitamin D deficiency which results in a breakdown in blood calcium regulation with concommitant hypocalcemia and bone calcium wasting.

It has been disclosed (*Holick, M.,* talk presented at the May 1979 Meetings of the American Society for Clinical Investigation in Washington, D.C., U.S.A., published in: Transactions of the Association of American Physicians, Vol. xcii, 54–63 (1979) and in "Molecular Endocrinology;" MacIntyre and Szelke, eds; Elsevier/North Holland Biomedical Press (1979), 301–308) that topical application of hydroxylated metabolites of vitamin D or hydroxylated provitamin D compounds to the skin combined with U.V. phototherapy is a method for the sustained administration of vitamin D metabolites to patients who suffer vitamin D metabolic disorders. When the hydroxylated provitamins are applied and irradiated with ultraviolet radiation, they convert to hydroxylated previtamins which then thermally isomerize to the hydroxylated vitamin D. This work is also disclosed in *Holick et al,* New England J. of Med., 303: 349–354 (1980) and co-pending U.S. Application Serial Number 022,393 filed March 21, 1979, by Holick and Uskokovic at the U.S. Patent and Trademark Office.

Hungarian Pat. No. 102,939 to Pless discloses cosmetic creams containing vitamin D precursors (such as ergosterol) which, when irradiated with ultraviolet rays, are transformed into vitamin D. U.S. Pat. 2,060,228 to Lorenz discloses soap compositions containing sterols, which have previously been irradiated to render the resulting sterols anti-rachitic.

The Holick, Pless and Lorenz disclosures, however, deal solely with the application and administration of (hydroxylated) provitamins or vitamin D in standard transparent carriers comprising fatty acid alcohols, semisolid petroleum hydrocarbons, 1, 2-glycols, emulsifying agents, methyl celluloses, polyoxyethylene glycols, or the like.

Leigh, U.S. Pat. No. 3,981,996, discusses pharmaceutical skin compositions comprising a hydrophobic medium, a water-insoluble powder dispersed therein and a medicament absorbed on the powder. It is suggested that among the medicaments, a sun screening preparation comprising vitamin D can be used.

Any attempt to add vitamin D into a sunscreening composition, such as that of Leigh, however, has to take into account the possibility of uncontrolled increased absorption of vitamin D, with concomittant loss of concentration control, and the appearance of side effects such as vitamin D toxicity leading to hypercalcemic states.

A need therefore, continues to exist for sunscreening compositions possessing high absorption properties in the ultraviolet region particularly around 250–320 nm, while superposing on the sunburn curve, and simultaneously not preventing the undesirable loss of the cutaneous photoproduction of previtamin.

SUMMARY OF THE INVENTION

It is therefore an object of the invention to provide a sunscreen composition having high absorption properties in the ultraviolet region, and particularly one which compensates for the block in the natural synthesis of previtamin due to the sunscreen.

This and other objects of the invention as will hereinafter become more readily apparent, have been attained by providing a sunscreening composition comprising:

a sunscreening amount of an opacifying agent and a therapeutic amount of a $\Delta^{5,7}$ steroidal diene which, is non-hydroxylated at any of positions 1; 1,25;1,24,25;1,25,26 thereof.

DESCRIPTION OF THE PREFERRED EMBODIMENTS

The sunscreening agents useful in the present invention can be any of the opacifying agents well-known to the art for this purpose. These compounds have high absorbance properties at 290–320 nm and superimpose on the sunburn curve. They are non-toxic and compatible with the skin. Among them may be listed, for example:

ethyl p-amino benzoate (benzocaine);
p-amino benzoic acid (PABA);
phenyl selicylate (salol);
2-ethoxyethyl p-methoxy cinnamate;
glyceryl p-aminobenzoate;
2, 4-dibenzoyl resorcinol;
octyl dimethyl PABA;
oxybenzone;
octyl methoxycinnamate;
benzophenones;
menthyl antranilate;
cinoxate;
amyldimethyl PABA;
homomentyl salicylate;
digalloyl trioleate;
ethyl-p-glycosylimido benzoate;
Red veterinary petrolatum.

For other examples, see also; Algra, R.J. et al, Int. J. Derm. 17; 628–634 (1978); Sayre, R. M. et al, Photochemistry and Photobiology 29; 559–566 (1979). One or more of these opacifying agents are mixed with a $\Delta^{5,7}$ steroidal diene which is a provitamin D. The $\Delta^{5,7}$ steroidal dienes are substituted by appropriate functional groups so that they are capable, upon photolysis at 250–320 nm, especially 255–310 nm, of cleavage of the 9–10 bond thereof, to yield a previtamin D derivative which, in turn, is capable, upon thermal isomerization, via an antarafacial 1,7-sigmatropic shift to be converted to a compound that requires further metabolic activation before it becomes biologically active, i.e. to a compound that becomes hypocalcemically active and capable of maintaining Ca and P homeostasis. When a provitamin D is photolyzed to yield a previtamin D, which in turn, by a skin mediated thermal reaction isomerizes to a vitamin D, the latter may or may not be immediately hypocalcemically active. It is known that the biologically active form of vitamin $D_3$ is the hydroxylated metabolite thereof, 1,25 dihydroxyvitamin $D_3$. Thus, if the $\Delta 5,7$ steroidal dienes of the invention are hydroxylated at positions 1 and 25, the resulting vitamin $D_3$ will be immediately biologically active. However, in this invention the $\Delta^{5,7}$ steroidal dienes are not hydroxylated at active or potentially active positions 1;1,25; 1,24,25; 1,25,26 so that the resulting vitamins $D_3$ must still by hydroxylated by normal metabolic processes, to become active. The problems with using provitamins hydroxylated at positions 1; 1,25; 1,24,25 or 1,25,26 in the sunscreening compositions of the invention is that once the hydroxylated vitamin $D_3$ is formed by photolysis and thermal rearrangement it will act directly, since its transport through the skin and blood stream onto the site of action is very fast. This is an advantage in the therapeutic treatment of individuals with metabolic hydroxylation deficiencies. Such therapy is, of course, under close medical supervision in order to prevent active vitamin $D_3$ overdosage. In a sunscreening composition which is being applied by laymen/women several times daily, without medical supervision, overdosage might be a serious problem. Thus, the hydroxylated provitamins are not desired in this invention. By utilizing $\Delta^{5,7}$ steroids not hydroxylated at positions 1; 1,25; 1,24,25 or 1,25,26, it is possible to take full advantage of the beneficial regulatory mechanisms brought about by normal liver and kidney functions. Thus, a slow, steady supply of biologically active metabolite is assured, regardless of the amount of precursor used by the sunbather. Another natural regulatory mechanism taken advantage of in the present invention is that provided by the photoequilibrium between previtamin $D_3$, and tachysterol (or a tachysterol-like derivative) and lumisterol (or a lumisterol-like derivative). FIG. 1 shows this equilibrium for the transformation of 7-dehydrocholesterol into previtamin $D_3$ and the partition of previtamin $D_3$ into three compounds: vitamin $D_3$ (by skin mediated thermal isomerization), and two biologically inert compounds: lumisterol or tachysterol (by further sun-mediated photochemical ring closure and isomerization). Lumisterol and tachysterol serve as "storage" compounds for the formation, by reversal of the photoequilibrium, of further previtamin $D_3$. Vitamin $D_3$ is carried into the bloodstream and through the blood to its sites of normal hydroxylation by vitamin $D_3$ binding protein (DBP). The combination of liver and kidney hydroxylation and the photoequilibrium reactions on the skin provide a natural regulatory mechanism for vitamin $D_3$ supply to the organism.

By using vitamin D precursors in sunscreening compositions according to the invention, it is possible for the first time to simultaneously control the blockage of harmful ultraviolet radiation, while preventing harmful vitamin $D_3$ depletion. The sunscreening compositions of the present invention are therefore therapeutic.

The word "steroid" has a well-defined meaning to those skilled in the art. Thus, for example, Morrison and Boyd, "Organic Chemistry," 3rd Ed., 1973, at page 514, define a steroid as a molecule having the following formula (given here with the ring numbering and lettering system)(3):

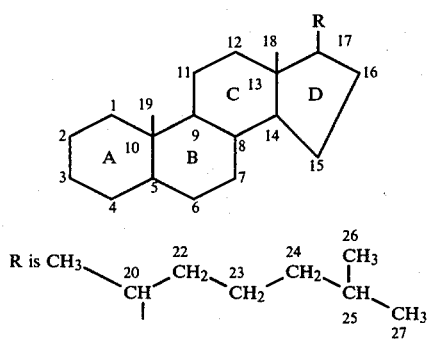

In the present invention, $\Delta^{5,7}$ steroidal dienes are used, having the following generalized formula (4):

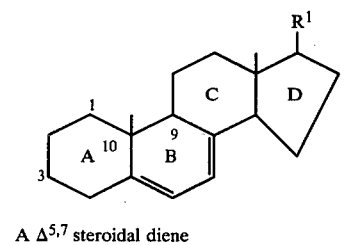

A $\Delta^{5,7}$ steroidal diene

In this formula, $R^1$ may either be a fully unsubstituted $C_7$ aliphatic chain, as defined for R above, or $R^1$ may be as defined below.

The steroidal dienes used in this invention are so called provitamin precursors of biologically active vitamin D. By a sequence of transformations the steroidal dienes are first photochemically cleaved at the 9, 10 bond of ring B to yield a closer precursor of the final vitamin D product. This ring-opened precursor is normally called "previtamin D" in the vitamin D literature (see for example, Napoli, J. L. and DeLuca, H. F., "Blood Calcium Regulators," which is Chapter 26 in Burger's Medicinal Chemistry, 4th edition, Part II, Wiley Interscience 1979, specifically at page 728). This first photochemical transformation is shown in equation 5:

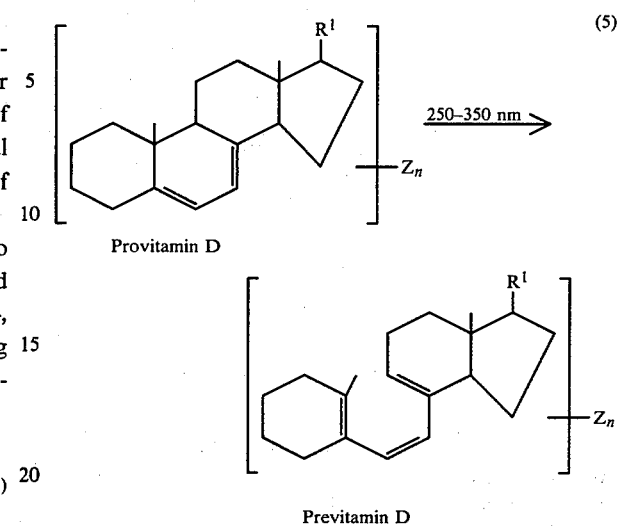

$Z_n$ represents one or more, same or different substituents which do not interfere with the photochemical transformation of the $\Delta^{5,7}$ steroidal provitamin to previtamin D, which do not interfere with the subsequent thermal and/or hydrolytic transformations of previtamin D to the vitamin D derivative, or with the necessary metabolic transformations (e.g. hydroxylations) thereof, and which do not interfere with the biological action of the final vitamin D metabolite, with the proviso, however, that $Z_n$ is not a hydroxy group at positions 1, 24, 25 or 26.

Such substituents $Z_n$ may, for example, be hydroxy groups, lower alkoxy or alkyl groups, acyloxy groups, carbonyloxy groups, halogens such as fluorine, chlorine or bromine, ether groups, such as lower alkyl ethers, amines, lower acyl amines, aryloxy groups, and the like.

It is known (De Luca, supra, page 728) that previtamin $D_3$ and its derivatives are only slowly converted to vitamin $D_3$ at physiological temperatures by a thermal antarafacial 1,7-sigmatropic shift. The previtamin D derivatives formed photochemically in the present invention therefore should be capable of undergoing such thermal isomerization in order to yield a vitamin D derivative, which can be metabolized by hydroxylation to be physiologically active. The thermal isomerization of previtamin D to vitamin D derivatives or precursors thereof, is shown in equation 6:

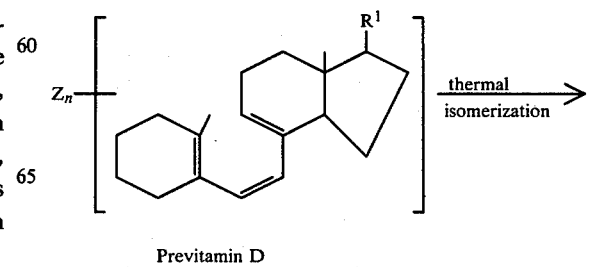

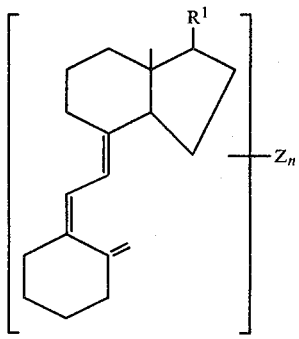

Vitamin D derivative
or precursor thereof

When ester or carbonate derivatives are used as the $\Delta^{5,7}$ steroidal dienes, the resulting vitamin D may be an ester or carbonate or other hydrolytically unstable precursor. Hydrolysis to liberate the potentially active (by further hydroxylative metabolism) form of the vitamin D will then occur under normal conditions at physiological temperature either enzymatically or non-enzymatically. The two- or three-step process, including the photochemical transformation, the thermal isomerization and possible hydrolytic reaction, provides a steady supply of vitamin to the organism by absorption through the skin. Absorption through the skin may occur at the level of the previtamin D or at the level of the vitamin D derivative or hydrolytic precursor thereof. $\Delta^{5,7}$ steroidal provitamins D are not normally substantially absorbed through the skin. Thus, by using a large excess of steroidal diene in a sunscreening composition, blockage of harmful ultraviolet radiation is assured, while small amounts of vitamin D or its precursors are steadily absorbed through the epidermis for further metabolism.

Among the preferred substituted $\Delta^{5,7}$ steroidal dienes used as sunscreen compounds in the present invention are those of the following formula (7):

wherein Y is hydrogen, lower alkyl or lower acyl; $R_2$ is hydrogen or an acyl or carbonate group; and the bond between carbons 22 and 23 may be single or double.

In this formula, the stereochemistry of the ring substituents may either be $\alpha$ (going behind the plane of the paper) or $\beta$ (coming out of the plane of the paper). Alternatively, mixtures of stereoisomers can also be used.

Among further preferred compounds are those wherein Y=hydrogen; $R_2$=hydrogen and the bond between carbons 22 and 23 is a single bond. In such case, the resulting vitamin obtained after photolytic and thermal reactions is vitamin $D_3$. Most preferably the hydroxy group at position 3 is in the $\beta$ configuration.

When $R_2$ is an acyl group, such as, for example, a lower acyl group, the vitamin D derivative is a hydrolytically labile precursor of vitamin D. As mentioned previously, the hydrolysis to yield the potentially active derivative can either be non-enzymatic or enzymatic, either on the skin surface or after the precursor has been absorbed therethrough. Among the preferred acyl groups are the $C_1-C_{20}$ saturated or unsaturated, substituted or unsubstituted, acyl groups, preferably unsubstituted lower alkyl acyl groups. Aroyl groups can also be used in the present invention, such as benzoyl, or substituted benzoyl, wherein the substituent may be any of the previously described substituents.

Among preferred $R^2$ groups are those which carry a sunscreening agent as the main residue. Thus, such compounds are conjugates (through esterification) of a $\Delta^{5,7}$ steroidal diene and a sunscreening compound. Upon hydrolysis, the ester splits into its acid component (sunscreen) and its alcohol component (hydroxylated pro, pre- or vitamin D). The acyl components may be, for example:

p-aminobenzoyl;
o-hydroxy benzoyl; anthranoyl;
p-methoxy cinnamoyl;

and the like. Any substituents on the steroid in such case need, in addition, the requirement that they do not interfere with the hydrolysis of the ester group.

Among the acyl or carbonate derivatives it is possible to use those of the following formula (8);

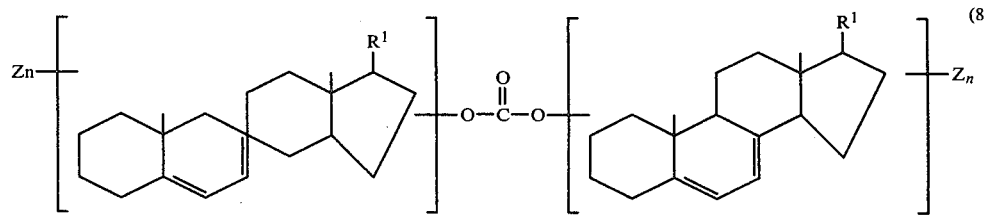

(8)

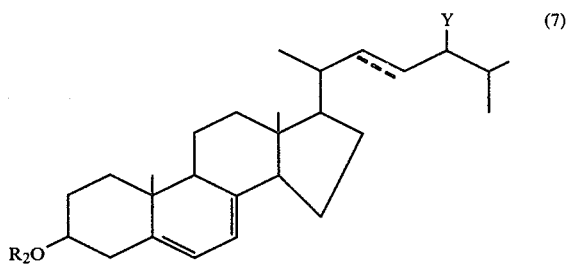

(7)

wherein the carbonate group bridges two $\Delta^{5,7}$ steroidal diene molecules by two hydroxy groups respectively. In this case each molecule in the dimer will undergo photochemical ring opening to the previtamin D derivatives, followed by thermal isomerization to the vitamin D precursors. Upon hydrolysis of the carbonate, two moles of potentially biologically active vitamin D are obtained, for further metabolism.

The general and specificy synthesis of $\Delta^{5,7}$ steroidal dienes is well known in the art. See, for example, *Dauben et al*, Journal of the American Chemical Society, Vol. 75, pp. 3255-3258 (1953); *Dauben, ibid,* Vol. 73:4496 (1951); *Bernstein et al, ibid,* Vol. 75: 1480-1481 (1953); or *Dauben et al,* U.S. Pat. No. 2,926,163. This latter patent teaches specifically the preparation of $\Delta^{5,7}$ 3-hydroxy steroids, which are among the preferred compounds of the present invention. See also, *Semmler, E.J. et al,* Tetrahedron Letters, 40:4147–4150 (1972); *Kaneko, C., et al;* Steroids 23:75–92 (1974); *Lam, H.Y. et al,* Biochemistry 12:4851–4855 (1973); *Barton, D.H.R. et al,* J. Amer.-Chem. Soc, 95:2748–2749 (1973); *Holick, M.F., et al,* J. Biol. Chem. 250:226–230 1975 (provitamin intermediates carrying a variety of reactive subsituents at C-22, as intermediates for a large number of provitamins); *Salmond, W.D.,* in "Vitamin D, Basic Research and Its Clinical Application," Proceedings of the 4th Workshop on Vitamin D, Berlin, West Germany, February 1979, Norman, A.W., et al, editors, New York 1979, pp. 25–31 (stigmasterol as starting material for a variety of provitamin D₃ deviatives); *Ikekawa, N., et al.* ibid, pp. 13–19 (synthesis of methoxy, and halo provitamins); *Salmond, W.D.,* ibid, pp. 62–70 (provitamins with a variety of side chains); *Crump, D.R., et al,* J. Chem. Soc., Perkin I, 1973, 2731–2733; *Stewart, W.D.,* "Algal Physiology and Biochemistry," Chapter 9, 266–280 (1974) (sterols from algae)

The compositions of the present invention may require a cosmetologically inert carrier in addition to the sunscreening compound. This carrier may be a solvent such as water, glycerol, alcohol, propylene glycol, fatty alcohols, triglycerides, fatty acid esters or mineral oils. Other possible carriers are liquid petrolatum (Nujol), isopropyl palmitate polyethyleneglycol, ethanol 95%, polyoxyethylenemonolaurate 5% in water, sodium lauryl sulfate 5% in water. Any other normally used sunscreen carrier can, of course, be used in the present invention. Other materials, such as antioxidants, humectants, viscosity stabilizers and the like may be added if necessary. The $\Delta^{5,7}$-steroidal diene of the present invention may be present in an amount sufficient to provide therapeutic action upon further reactions and metabolism.

The sunscreening compositions can be liquids or pastes of different viscosity. When the composition is liquid it may contain 0.01–50.0% by weight of the $\Delta^{5,7}$ steroids, with the remainder being the carrier, the sunscreening opacifying agent, antioxidants, emulsifiers, and the like. Preferably the range is 0.05%–5% by weight. When the composition is an ointment or cream or paste, the $\Delta^{5,7}$ steroids are present in 0.01–50.0% by weight preferably 0.05–1%. Although it is envisioned that the compositions of the present invention may successfully be used as sunscreening lotions for beach use, or sport activities (such as hiking, bicycling, saiing, etc.), it is, of course, also possible to use the compositions of the invention for indoor suntanning activities, such as those carried out with suntanning lamps.

The sunscreening compositions of the invention should be applied so that at least 1 microgram preferably at least 100 micrograms of the $\Delta^{5,7}$ steroidal diene is administered to the skin per cm². In general, no more than about 100 mg/cm² of $\Delta^{5,7}$ steroid would be needed for therapeutic action. This is especially true since through the application of those materials to the skin, the amount of potentially biologically active material transported to the blood stream is regulated and stored in the skin, and the amount of active material is regulated by the liver and kidney. Therefore, the danger of applying vitamin D₃, biologically active vitamin D materials or hydroxylated provitamin D in excessive dosages is minimized through the controlled transport by the skin to the bloodstream of the non-biologically active vitamin D or previtamin, and its natural hydroxylation in the liver and kidney.

Having now generally described this invention, it will be apparent to one of ordinary skill in the art that the same can be carried out in a variety of embodiments and variations which are equivalent without affecting the spirit or scope of the invention or any embodiments thereof.

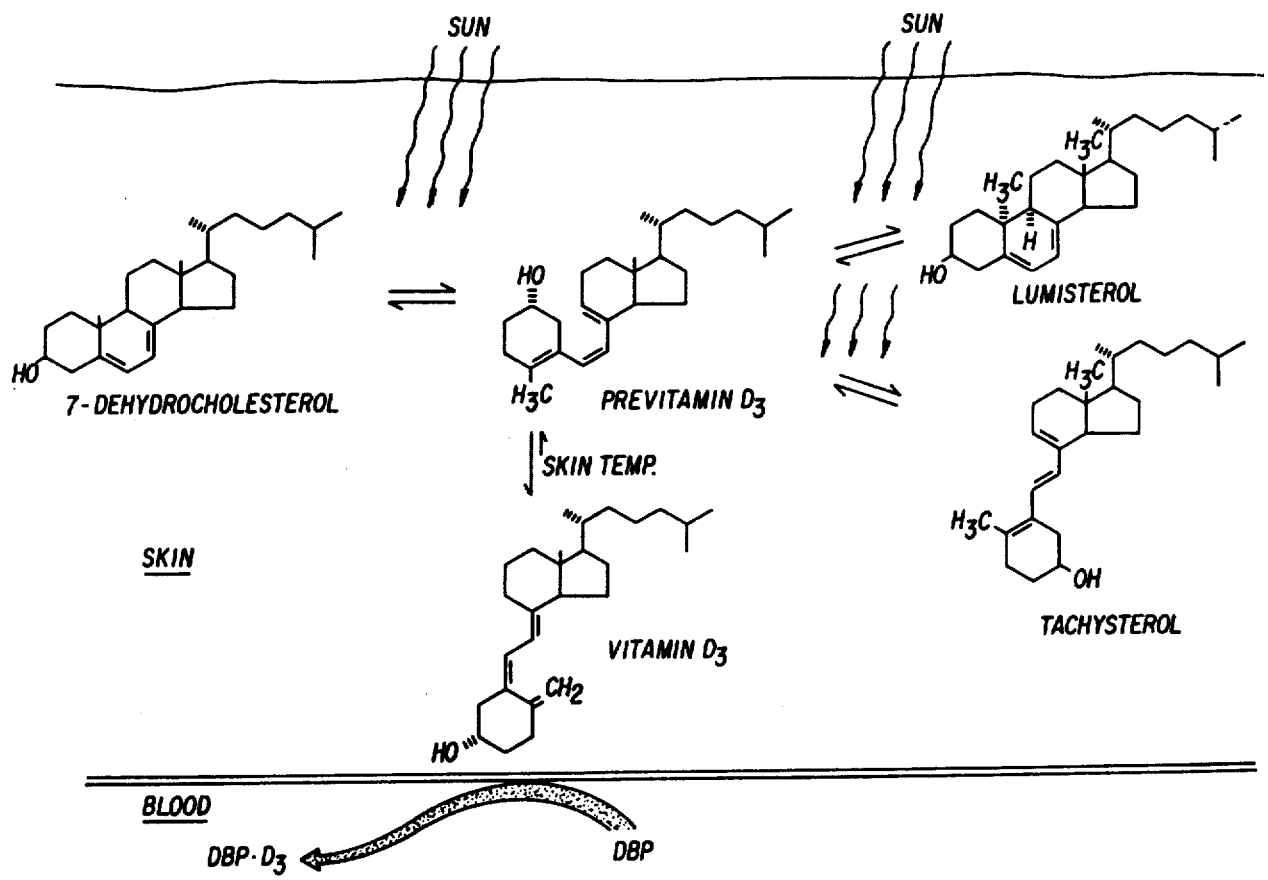

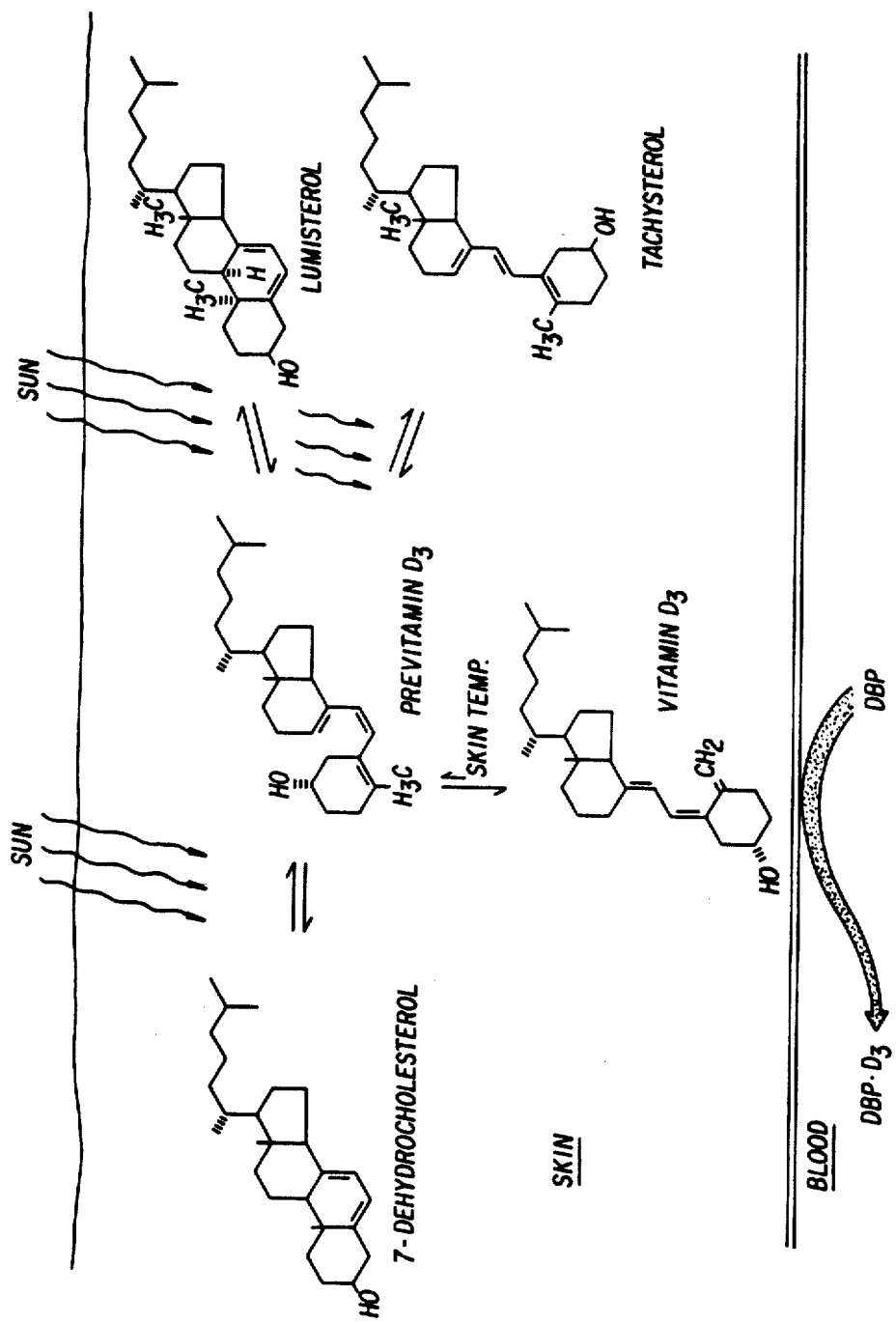

What is claimed as new and desired to be secured by Letters Patent of the United States is:

1. A sunscreening composition which comprises:
   a sunscreening amount of an opacifying agent having substantial absorbance at 250–320 nm; and
   0.01–50% by weight of the total composition of a substituted or unsubstituted $\Delta^{5,7}$ steroidal diene which is nonhydroxylated at any of positions 1; 1,25; 1, 24, 25 and 1, 25, 26 thereof; and having the formula:

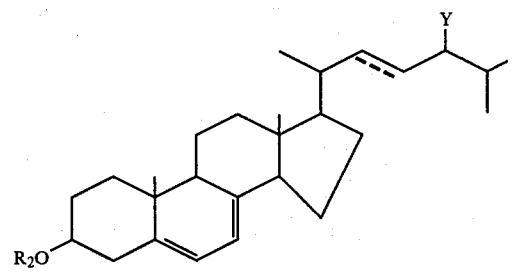

wherein Y is hydrogen or lower alkyl or acyl;
   R₂ is hydrogen or an acyl or carbonate group; and the bond between carbons 22 and 23 can be single or double.

2. The composition of claim 1, wherein in said $\Delta^{5,7}$ steroid Y is hydrogen, R₂ is hydrogen and the bond between carbons 22 and 23 is single.

3. The composition of any of claims 1 or 3, wherein said substituent R₂O— is in the β configuration.

4. The composition of claim 1, wherein R₂ is the acyl derivative of a sunscreening agent.

5. The composition of claim 4, wherein said derivative is p-aminobenzoyl.

6. The composition of claim 1 wherein said $\Delta^{5,7}$ steroidal diene is present in 0.05–5% by weight of the total composition.

7. A method of protecting the human skin from solar radiation which comprises applying to said skin a sunscreening amount of the composition of any of claims 1 or 3.

8. A sunscreening composition which comprises:
   a sunscreening amount of an opacifying agent having substantial absorbance at 250–320 nm;
   0.01–50% by weight of the composition, of a $\Delta^{5,7}$ steroidal diene which is capable of sequentially
   (a) undergoing photochemically induced cleavage at the C-9, C-10 bond thereof at 250–320 nm, to yield a previtamin D;
   (b) undergoing a thermally induced 1,7-antarafacial sigmatropic shift to yield a vitamin D precursor and
   (c) undergoing hydroxylation at positions 1,25 of said vitamin D precursor to yield a 1,25 dihydroxyvitamin D₃ derivative which is metabolically active in maintaining calcium and phosphorus homeostasis;
   with the proviso that said $\Delta^{5,7}$ steroidal diene is not hydroxylated at positions 1; 1, 25; 1,24,25; and 1,25, 26 thereof.

* * * * *

UNITED STATES PATENT AND TRADEMARK OFFICE
CERTIFICATE OF CORRECTION

PATENT NO. : 4,310,511
DATED : January 12, 1982
INVENTOR(S) : Michael F. Holick

It is certified that error appears in the above—identified patent and that said Letters Patent is hereby corrected as shown below:

Column 1, delete the formula and substitute therefor:

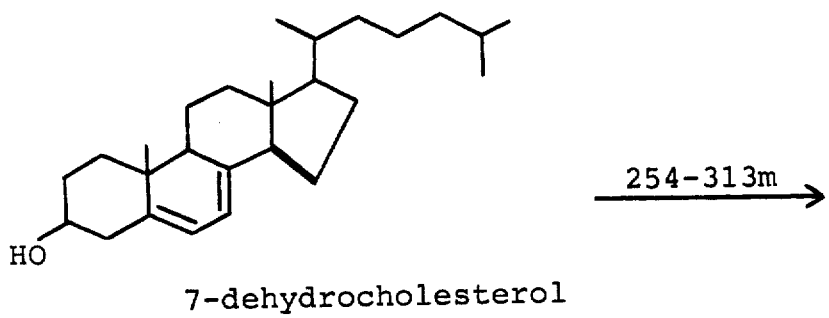

7-dehydrocholesterol

Column 4, line 23, delete "$\Delta 5,7$" and substitute therefor --$\Delta^{5,7}$--.

Column 4, line 28, delete "by" and substitute therefor --be--.

Column 8, line 63, delete "specificy" and substitute therefor --specific--.

UNITED STATES PATENT AND TRADEMARK OFFICE
CERTIFICATE OF CORRECTION

PATENT NO. : 4,310,511

DATED : January 12, 1982

INVENTOR(S) : Michael F. Holick

It is certified that error appears in the above–identified patent and that said Letters Patent are hereby corrected as shown below:

Column 9, line 16, delete "deviatives" and substitute therefor --derivatives--.

Column 10, line 37, in Claim 3, delete "Claims 1 or 3" and substitute therefor --Claims 1 or 2--.

Signed and Sealed this

Fourteenth Day of June 1983

[SEAL]

*Attest:*

DONALD J. QUIGG

*Attesting Officer*     *Acting Commissioner of Patents and Trademarks*

UNITED STATES PATENT AND TRADEMARK OFFICE
CERTIFICATE OF CORRECTION

PATENT NO. : 4,310,511

DATED : January 12, 1982

INVENTOR(S) : Michael F. Holick

Page 1 of 3

It is certified that error appears in the above-identified patent and that said Letters Patent is hereby corrected as shown below:

The title page and the sheet of drawing should appear as shown on the attached sheets.

*Signed and Sealed this*

*Twenty-eighth* Day of *August 1984*

[SEAL]

*Attest:*

*Attesting Officer*

GERALD J. MOSSINGHOFF

*Commissioner of Patents and Trademarks*

United States Patent [19]

Holick

[11] 4,310,511

[45] Jan. 12, 1982

[54] SUNSCREEN COMPOSITIONS CONTAINING $\Delta^{5,7}$ STEROIDAL DIENES

[75] Inventor: Michael F. Holick, Sudbury, Mass.

[73] Assignee: Massachusetts General Hospital, Boston, Mass.

[21] Appl. No.: 193,297

[22] Filed: Oct. 2, 1980

[51] Int. Cl.³ .................. C07J 7/00; A01N 45/00; A61K 7/42; A61K 7/44
[52] U.S. Cl. .................................. 424/59; 424/238; 424/60; 260/397.2
[58] Field of Search .................. 424/59, 238, 242; 260/397.2

[56] References Cited

U.S. PATENT DOCUMENTS 3,479,428 11/1969 Bryce et al. .................. 424/59
4,115,547 9/1978 Degen et al. .................. 424/59

FOREIGN PATENT DOCUMENTS 1540187 8/1968 France .................. 424/59

Primary Examiner—Elbert L. Roberts
Attorney, Agent, or Firm—Oblon, Fisher, Spivak, McClelland & Maier

[57] ABSTRACT

A sunscreening composition which comprises a sunscreening amount of an opacifying agent and a therapeutic amount of a $\Delta^{5,7}$ steroidal diene which is non-hydroxylated at any of positions 1; 1,25; 1,24,25 or 1,25,26 thereof.

8 Claims, 1 Drawing Figure